US006855492B2

(12) United States Patent
O'Hagan et al.

(10) Patent No.: US 6,855,492 B2
(45) Date of Patent: Feb. 15, 2005

(54) USE OF MICROPARTICLES COMBINED WITH SUBMICRON OIL-IN-WATER EMULSIONS

(75) Inventors: Derek O'Hagan, Berkeley, CA (US); Gary Van Nest, El Sobrante, CA (US); Gary S. Ott, Oakland, CA (US); Manmohan Singh, Hercules, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 10/211,025

(22) Filed: Aug. 2, 2002

(65) Prior Publication Data

US 2003/0082213 A1 May 1, 2003

Related U.S. Application Data

(60) Continuation of application No. 09/935,466, filed on Aug. 20, 2001, now Pat. No. 6,458,370, which is a continuation of application No. 09/564,416, filed on May 2, 2000, now Pat. No. 6,306,405, which is a division of application No. 09/015,736, filed on Jan. 29, 1998, now Pat. No. 6,086,901.
(60) Provisional application No. 60/069,724, filed on Dec. 16, 1997.

(51) Int. Cl.$^7$ ................................................ C12Q 1/00
(52) U.S. Cl. ................ 435/4; 435/5; 435/6; 424/278.1; 424/70.11; 424/70.19; 424/204.1
(58) Field of Search .......................... 424/278.1, 70.11, 424/70.19, 204.1; 435/4, 5, 6

(56) References Cited

U.S. PATENT DOCUMENTS

| | | | |
|---|---|---|---|
| 5,629,167 A | 5/1997 | Ratti | |
| 5,783,567 A | 7/1998 | Hedley et al. | |
| 5,869,103 A | 2/1999 | Yeh et al. | |
| 5,961,970 A | 10/1999 | Lowell et al. | |
| 6,086,901 A | 7/2000 | O'Hagan et al. | |
| 6,306,405 B1 * | 10/2001 | O'Hagan et al. | 424/278.1 |
| 6,458,370 B1 * | 10/2002 | O'Hagan et al. | 424/278.1 |

FOREIGN PATENT DOCUMENTS

| | | |
|---|---|---|
| EP | 0 399 843 B1 | 7/1994 |
| WO | WO 90/14837 | 12/1990 |
| WO | WO 92/00081 | 1/1992 |
| WO | WO 97/02810 | 1/1997 |

OTHER PUBLICATIONS

Esparza et al., "Parameters Affecting the Immunogenicity of Microencapsulated Tetanus Toxoid," *Vaccines* 10(10):714–720 (1992).

Fahey et al., Status of Immune–Based Therapies in HIV Infection and AIDS, Clin. Exp. Immunol. vol. 88, pp. 1–5, 1992.

A.S. Fauci, "Update on the Status of Vaccine Development," *Pediatric Aids and HIV Infection: Fetus to Adolescent* 5(1):47–58 (1994).

Fox, No Winners Against AIDS, Bio/Technology, vol. 12, p. 128, Feb. 1994.

Haynes et al., Update on the Issues of HIV Vaccine Development, The Finnish Medical Society, DUOCECIM, Ann. Med., vol. 28, pp. 39–41, 1996.

Higgins et al., "MF59 Adjuvant Enhances the Immunogenicity of Influenza Vaccine in Both Young and Old Mice," *Vaccine* 14(6):478–484 (1996).

Moore et al., "Immunization with a Soluble Recombinant HIV Protein Entrapped in Biodegradable Microparticles Induces HIV–Specific CD8$^+$Cytotoxic T Lymphocytes and CD4$^+$Th1 Cells," *Vaccine* 13(18):1741–1749 (1995).

O'Hagan et al., "Biodegradable Microparticles for Oral Immunization," *Vaccine* 11:149–154 (1993).

O'Hagan, "Recent Advances in Vaccine Adjuvants for Systemic and Mucosal Administration," *J. Pharm. Pharmacol* 49:1–10 (1997).

Ott et al., "MF59—Design and Evaluation of a Safe and Potent Adjuvant for Human Vaccines," *Vaccine Design: The Subunit and Adjuvant Approach* (Powell, M.F. and Newman, M.J. eds.) Plenum Press, New York, pp. 277–296 (1995).

Sanchez–Pescador et al., "The Effect of Adjuvants on the Efficacy of a Recombinant Herpes Simplex Virus Glycoprotein Vaccine," *The Journal of Immunol.* 141(5):1720–1727 (1988).

Vordermeier et al., "Synthetic Delivery System for Tuberculosis Vaccines: Immunological Evaluation of the *M. Tuberculosis* 38 kDa Protein Entrapped in Biodegradable PLG Microparticles," *Vaccine* 13(16):1576–1582 (1995).

* cited by examiner

*Primary Examiner*—Jeffrey Stucker
*Assistant Examiner*—Stacy B. Chen
(74) *Attorney, Agent, or Firm*—Roberta L. Robins; Michael J. Moran; Robert P. Blackburn

(57) ABSTRACT

Compositions are provided which include biodegradable microparticles with entrapped or adsorbed antigens, in combination with submicron oil-in-water emulsions. Also provided are methods of immunization which comprise administering to a vertebrate subject (a) a submicron oil-in-water emulsion, and (b) a therapeutically effective amount of a selected antigen entrapped in a microparticle.

15 Claims, 1 Drawing Sheet

USE OF MICROPARTICLES COMBINED WITH SUBMICRON OIL-IN-WATER EMULSIONS

CROSS-REFERENCE TO RELATED APPLICATIONS

This application is a continuation of U.S. patent application Ser. No. 09/935,466 filed Aug. 20, 2001, now U.S. Pat. No. 6,458,370, which is a continuation of U.S. patent application Ser. No. 09/564,416, filed May 2, 2000, now U.S. Pat. No. 6,306,405, which is a divisional of U.S. patent application Ser. No. 09/015,736, filed Jan. 29, 1998, now U.S. Pat. No. 6,086,901, from which applications priority is claimed pursuant to 35 U.S.C. §120 and this application is related to Provisional Patent Application Ser. No. 60/069,724, filed Dec. 16, 1997, from which priority is claimed under 35 U.S.C. §1 19(e)(1), and which applications are incorporated herein by reference in their entireties.

TECHNICAL FIELD

The present invention relates generally to vaccine compositions. In particular, the invention relates to the use of biodegradable microparticles including entrapped or adsorbed antigens, in combination with submicron oil-in-water emulsions.

BACKGROUND OF THE INVENTION

Numerous vaccine formulations which include attenuated pathogens or subunit protein antigens, have been developed. Conventional vaccine compositions often include immunological adjuvants to enhance immune responses. For example, depot adjuvants are frequently used which adsorb and/or precipitate administered antigens and which can retain the antigen at the injection site. Typical depot adjuvants include aluminum compounds and water-in-oil emulsions. However, depot adjuvants, although increasing antigenicity, often provoke severe persistent local reactions, such as granulomas, abscesses and scarring, when injected subcutaneously or intramuscularly. Other adjuvants, such as lipopolysacharrides, can elicit pyrogenic responses upon injection and/or Reiter's symptoms (influenza-like symptoms, generalized joint discomfort and sometimes anterior uveitis, arthritis and urethritis). Saponins, such as *Quillaja saponaria*, have also been used as immunological adjuvants in vaccine compositions against a variety of diseases.

More particularly, Complete Freund's adjuvant (CFA) is a powerful immunostimulatory agent that has been successfully used with many antigens on an experimental basis. CFA includes three components: a mineral oil, an emulsifying agent, and killed mycobacteria, such as *Mycobacterium tuberculosis*. Aqueous antigen solutions are mixed with these components to create a water-in-oil emulsion. Although effective as an adjuvant, CFA causes severe side effects primarily due to the presence of the mycobacterial component, including pain, abscess formation and fever. CFA, therefore, is not used in human and veterinary vaccines.

Incomplete Freund's adjuvant (IFA) is similar to CFA but does not include the bacterial component. IFA, while not approved for use in the United States, has been used elsewhere in human vaccines for influenza and polio and in veterinary vaccines for rabies, canine distemper and foot-and-mouth disease. However, evidence indicates that both the oil and emulsifier used in IFA can cause tumors in mice.

Muramyl dipeptide (MDP) has been found to be the minimal unit of the mycobacterial cell wall complex that generates the adjuvant activity observed with CFA. See, e.g., Ellouz et al., *Biochem. Biophys. Res. Commun.* (1974) 59:1317. Several synthetic analogs of MDP have been generated that exhibit a wide range of adjuvant potency and side effects. For a review of these analogs, see, Chedid et al., *Prog. Allergy* (1978) 25:63. Representative analogs of MDP include threonyl derivatives of MDP (Byars et al., *Vaccine* (1987) 5:223), n-butyl derivatives of MDP (Chedid et al., *Infect. Immun.* 35:417), and a lipophilic derivative of a muramyl tripeptide (Gisler et al., in *Inmmunomodulations of Microbial Products and Related Synthetic Compounds* (1981) Y. Yamamura and S. Kotani, eds., Excerpta Medica, Amsterdam, p. 167).

One lipophilic derivative of MDP is N-acetylmuramyl-L-alaflyl-D-isogluatminyl-L-alanine-2-(1'-2'-dipalmitoyl-sn-glycero3-hydroxyphosphoryloxy-ethylamine (MTP-PE). This muramyl tripeptide includes phospholipid tails that allow association of the hydrophobic portion of the molecule with a lipid environment while the muramyl peptide portion associates with the aqueous environment. Thus, the MTP-PE itself is able to act as an emulsifying agent to generate stable oil-in-water emulsions. MTP-PE has been used in an emulsion of 4% squalene with 0.008% TWEEN 80®, termed MTP-PE-LO (low oil), to deliver the herpes simplex virus gD antigen with effective results (Sanchez-Pescador et al., *J. Immunol.* (1988) 141:1720–1727), albeit poor physical stability. Recently, MF59, a safe, highly immunogenic, submicron oil-in-water emulsion which contains 4–5% w/v squalene, 0.5% w/v TWEEN 80®, 0.5% SPAN 85®, and optionally, varying amounts of MTP-PE, has been developed for use in vaccine compositions. See, e.g., Ott et al., "MF59—Design and Evaluation of a Safe and Potent Adjuvant for Human Vaccines" in *Vaccine Design: The Subunit and Adjuvant Approach* (Powell, M. F. and Newman, M. J. eds.) Plenum Press, New York, 1995, pp. 277–296.

Despite the presence of such adjuvants, conventional vaccines often fail to provide adequate protection against the targeted pathogen. In this regard, there is growing evidence that vaccination against intracellular pathogens, such as a number of viruses, should target both the cellular and humoral arms of the immune system.

More particularly, cytotoxic T-lymphocytes (CTLs) play an important role in cell-mediated immune defense against intracellular pathogens such as viruses and tumor-specific antigens produced by malignant cells. CTLs mediate cytotoxicity of virally infected cells by recognizing viral determinants in conjunction with class I MHC molecules displayed by the infected cells. Cytoplasmic expression of proteins is a prerequisite for class I MHC processing and presentation of antigenic peptides to CTLs. However, immunization with killed or attenuated viruses often fails to produce the CTLs necessary to curb intracellular infection. Furthermore, conventional vaccination techniques against viruses displaying marked genetic heterogeneity and/or rapid mutation rates that facilitate selection of immune escape variants, such as HIV or influenza, are problematic. Accordingly, alternative techniques for vaccination have been developed.

Particulate carriers with adsorbed or entrapped antigens have been used in an attempt to elicit adequate immune responses. Such carriers present multiple copies of a selected antigen to the immune system and promote trapping and retention of antigens in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG. Polymethyl methacrylate polymers are nondegradable while PLG particles biodegrade by random nonenzymatic hydrolysis of ester bonds to lactic and glycolic acids which are excreted along normal metabolic pathways.

Recent studies have shown that PLG microparticles with entrapped antigens are able to elicit cell-mediated immunity. For example, microencapsulated human immunodeficiency virus (HIV) gp120 has been shown to induce HIV-specific CD4+ and CD8+ T-cell responses in mice (Moore et al., *Vaccine* (1995) 13:1741–1749). Similarly, microparticle-encapsulated ovalbumin has been shown to be capable of priming cellular immune responses in vivo and can induce mucosal IgA responses when administered orally (O'Hagan et al., *Vaccine* (1993) 11:149–154). Additionally, both antibody and T-cell responses have been induced in mice vaccinated with a PLG-entrapped *Mycobacterium tuberculosis* antigen (Vordermeier et al., *Vaccine* (1995) 13:1576–1582). Antigen-specific CTL responses have also been induced in mice using a microencapsulated short synthetic peptide from the circumsporozoite protein of *Plasmodium berghei*.

However, the use of microparticles with entrapped or adsorbed antigen, in combination with submicron oil-in-water emulsions, has not heretofore been described.

DISCLOSURE OF THE INVENTION

The present invention is based on the surprising and unexpected discovery that the use of biodegradable microparticles, such as those derived from a poly((α-hydroxy acid), and including entrapped or adsorbed antigen, in combination with submicron oil-in-water emulsions, serves to enhance the immunogenicity of the antigen. The use of such combinations provides a safe and effective approach for enhancing the immunogenicity of a wide variety of antigens.

Accordingly, in one embodiment, the invention is directed to a composition comprising a submicron oil-in-water emulsion, and a selected antigen entrapped in, or adsorbed to, a biodegradable microparticle.

In another embodiment, the invention is directed to a composition comprising (a) a submicron oil-in-water emulsion which comprises 4–5% w/v squalene, 0.25–0.5% w/v TWEEN 80®, and 0.5% w/v SPAN 85®, and optionally, N-acetylmuramyl-L-alanyl-D-isogluatminyl-L-alanine-2-(1'-2-dipalmitoyl-sn-glycero-3-hydroxyphosphoryloxy-ethylamine, and (b) a selected antigen entrapped in, or adsorbed to, a biodegradable microparticle.

In yet another embodiment, the subject invention is directed to a method of immunization which comprises administering to a vertebrate subject (a) a submicron oil-in-water emulsion, and (b) a therapeutically effective amount of a selected antigen entrapped in, or adsorbed to, a biodegradable microparticle.

In still further embodiments, the invention is directed to a method of making a composition comprising combining a submicron oil-in-water emulsion with a selected antigen entrapped in, or adsorbed to, a biodegradable microparticle.

In particularly preferred embodiments, the microparticle is derived from a poly(α-hydroxy acid), preferably poly(L-lactide), poly(D,L-lactide) or poly(D,L-lactide-co-glycolide).

These and other embodiments of the present invention will readily occur to those of ordinary skill in the art in view of the disclosure herein.

DETAILED DESCRIPTION OF THE INVENTION

Figure 1:
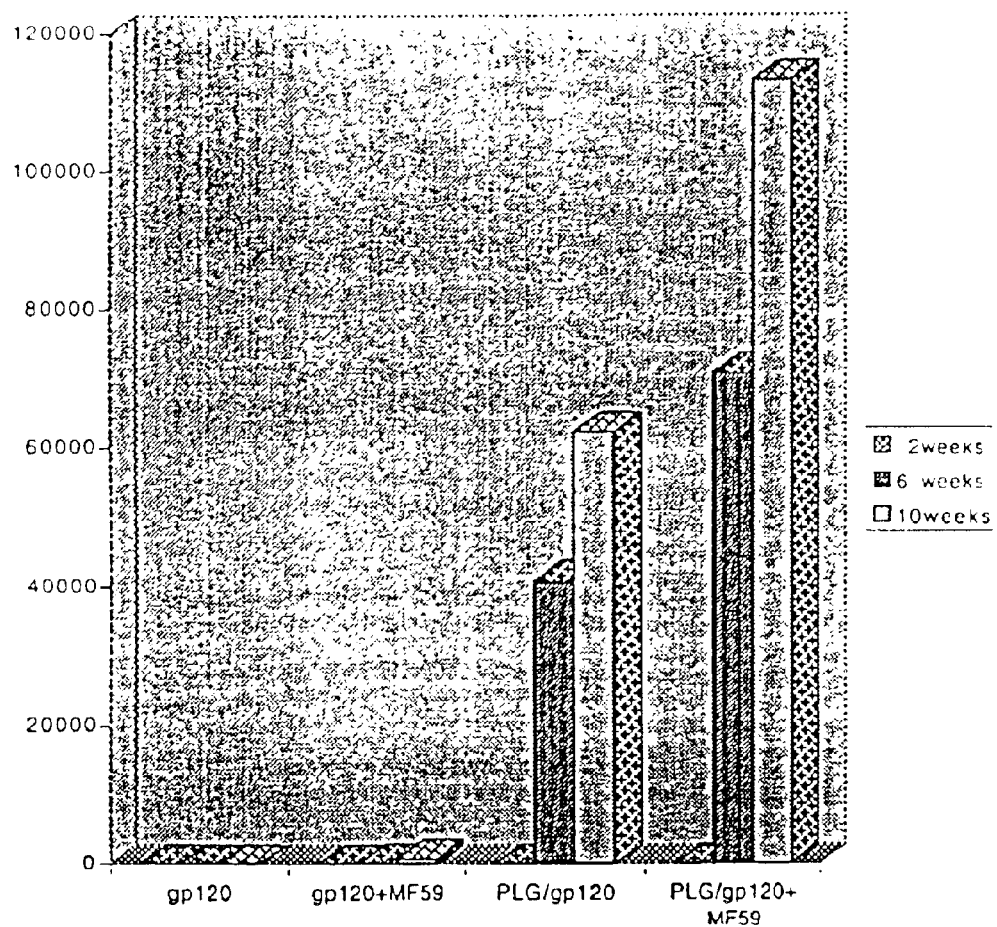
FIG. 1 shows total IgG titers at 2, 6 and 10 weeks following initial vaccination in mice immunized with gp120; gp120+MF59; PLG with entrapped gp120; and PLG with entrapped gp120+MF59.

The practice of the present invention will employ, unless otherwise indicated, conventional methods of chemistry, biochemistry, molecular biology, immunology and pharmacology, within the skill of the art. Such techniques are explained fully in the literature. See, e.g., *Remington's Pharmaceutical Sciences*, 18th Edition (Easton, Pa.: Mack Publishing Company, 1990); *Methods In Enzymology* (S. Colowick and N. Kaplan, eds., Academic Press, Inc.); and *Handbook of Experimental Immunology*, Vols. I-IV (D. M. Weir and C. C. Blackwell, eds., 1986, Blackwell Scientific Publications); and Sambrook, et al., *Molecular Cloning: A Laboratory Manual* (2nd Edition, 1989).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

I. Definitions

In describing the present invention, the following terms will be employed, and are intended to be defined as indicated below.

The term "microparticle" as used herein, refers to a particle of about 100 nm to about 150 μm in diameter, more preferably about 200 nm to about 30 μm in diameter, and most preferably about 500 nm to about 10 μm in diameter. Preferably, the microparticle will be of a diameter that permits parenteral administration without occluding needles and capillaries. Microparticle size is readily determined by techniques well known in the art, such as photon correlation spectroscopy, laser diffractometry and/or scanning electron microscopy. Microparticles for use herein will be formed from materials that are sterilizable, non-toxic and biodegradable. Such materials include, without limitation, poly (α-hydroxy acid), polyhydroxybutyric acid, polycaprolactone, polyorthoester, polyanhydride. Preferably, microparticles for use with the present invention are derived from a poly(α-hydroxy acid), in particular, from a poly(lactide) ("PLA") or a copolymer of D,L-lactide and glycolide or glycolic acid, such as a poly(D,L-lactide-co-glycolide) ("PLG" or "PLGA"), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the coadministered antigen. These parameters are discussed more fully below.

By "antigen" is meant a molecule which contains one or more epitopes that will stimulate a host's immune system to make a cellular antigen-specific immune response when the antigen is presented, or a humoral antibody response. Normally, an epitope will include between about 3–15, generally about 5–15, amino acids. For purposes of the present invention, antigens can be derived from any of several known viruses, bacteria, parasites and fungi. The term also intends any of the various tumor antigens. Furthermore, for purposes of the present invention, an "antigen" refers to a protein which includes modifications, such as deletions, additions and substitutions (generally conservative in nature), to the native sequence, so long as the protein maintains the ability to elicit an immunological response. These modifications may be deliberate, as through site-directed mutagenesis, or may be accidental, such as through mutations of hosts which produce the antigens.

An "immunological response" to an antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen or composition to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189–4199; Doe et al., *Eur. J. Immunol.* (1994) 24:2369–2376; and the examples below.

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

A vaccine composition which contains a selected antigen entrapped or adsorbed with a microparticle, along with a submicron oil-in-water emulsion adjuvant, or a vaccine composition containing an antigen entrapped or adsorbed with a microparticle which is coadministered with the subject submicron oil-in-water emulsion adjuvant, displays "enhanced immunogenicity" when it possesses a greater capacity to elicit an immune response than the immune response elicited by an equivalent amount of the microparticle/antigen without the submicron oil-in-water emulsion adjuvant. Thus, a vaccine composition may display "enhanced immunogenicity" because the antigen is more strongly immunogenic or because a lower dose of antigen is necessary to achieve an immune response in the subject to which it is administered. Such enhanced immunogenicity can be determined by administering the microparticle/antigen composition and submicron oil-in-water emulsion, and microparticle/antigen controls to animals and comparing antibody titers against the two using standard assays such as radioimmunoassay and ELISAs, well known in the art.

The terms "effective amount" or "pharmaceutically effective amount" of an agent, as provided herein, refer to a nontoxic but sufficient amount of the agent to provide the desired immunological response and corresponding therapeutic effect. As will be pointed out below, the exact amount required will vary from subject to subject, depending on the species, age, and general condition of the subject, the severity of the condition being treated, and the particular antigen of interest, mode of administration, and the like. An appropriate "effective" amount in any individual case may be determined by one of ordinary skill in the art using routine experimentation.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

By "pharmaceutically acceptable" or "pharmacologically acceptable" is meant a material which is not biologically or otherwise undesirable, i.e., the material may be administered to an individual along with the microparticle adjuvant formulations without causing any undesirable biological effects or interacting in a deleterious manner with any of the components of the composition in which it is contained.

By "physiological pH" or a "pH in the physiological range" is meant a pH in the range of approximately 7.2 to 8.0 inclusive, more typically in the range of approximately 7.2 to 7.6 inclusive.

By "vertebrate subject" is meant any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species, since the immune systems of all of these vertebrates operate similarly.

II. Modes of Carrying Out the Invention

The present invention is based on the discovery that the use of microparticles with entrapped or adsorbed antigen, in combination with submicron oil-in-water emulsions, provide a vigorous immune response, even when the antigen is by itself weakly immunogenic. The submicron oil-in-water adjuvants of the present invention can be incorporated into vaccine compositions containing the desired microparticle/ antigen, or can be administered separately, either simultaneously with, just prior to, or subsequent to, a microparticle/antigen-containing composition. Furthermore, the formulations of the invention may be used to enhance the activity of antigens produced in vivo, i.e., in conjunction with DNA immunization.

Although the individual components of the vaccine compositions and methods described herein were known, it was unexpected and surprising that such combinations would enhance the efficiency of antigens beyond levels achieved when the components were used separately.

The method of the invention provides for cell-mediated immunity, and/or humoral antibody responses. Thus, in addition to a conventional antibody response, the system herein described can provide for, e.g., the association of the expressed antigens with class I MHC molecules such that an in vivo cellular immune response to the antigen of interest can be mounted which stimulates the production of CTLs to allow for future recognition of the antigen. Furthermore, the methods may elicit an antigen-specific response by helper T-cells. Accordingly, the methods of the present invention will find use with any antigen for which cellular and/or humoral immune responses are desired, including antigens derived from viral, bacterial, fungal and parasitic pathogens that may induce antibodies, T-cell helper epitopes and T-cell cytotoxic epitopes. Such antigens include, but are not limited to, those encoded by human and animal viruses and can correspond to either structural or non-structural proteins.

The technique is particularly useful for immunization against intracellular viruses and tumor cell antigens which normally elicit poor immune responses. For example, the present invention will find use for stimulating an immune response against a wide variety of proteins from the herpesvirus family, including proteins derived from herpes simplex virus (HSV) types 1 and 2, such as HSV-1 and HSV-2 glycoproteins gB, gD and gH; antigens derived from varicella zoster virus (VZV), Epstein-Barr virus (EBV) and cytomegalovirus (CMV) including CMV gB and gH; and antigens derived from other human herpesviruses such as HHV6 and HHV7. (See, e.g. Chee et al., *Cytomegaloviruses* (J. K. McDougall, ed., Springer-Verlag 1990) pp. 125–169, for a review of the protein coding content of cytomegalovirus; McGeoch et al., *J. Gen. Virol.* (1988) 69:1531–1574, for a discussion of the various HSV-1 encoded proteins; U.S. Pat. No. 5,171,568 for a discussion of HSV-1 and HSV-2 gB and gD proteins and the genes encoding therefor; Baer et al., *Nature* (1984) 310:207–211, for the identification of protein coding sequences in an EBV genome; and Davison and Scott, *J. Gen. Virol.* (1986) 67:1759–1816, for a review of VZV.)

Antigens from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV), can also be conveniently used in the techniques described herein. By way of example, the viral genomic sequence of HCV is known, as are methods for obtaining the sequence. See, e.g., International Publication Nos. WO 89/04669; WO 90/11089; and WO 90/14436. The HCV genome encodes several viral proteins, including E1 (also known as E) and E2 (also known as E2/NS1) and an N-terminal nucleocapsid protein (termed "core") (see, Houghton et al., *Hepatology* (1991) 14:381–388, for a discussion of HCV proteins, including E1 and E2). Each of these proteins, as well as antigenic fragments thereof, will find use in the present methods. Similarly, the sequence for the δ-antigen from HDV is known (see, e.g., U.S. Pat. No. 5,378,814) and this antigen can also be conveniently used in the present methods. Additionally, antigens derived from HBV, such as the core antigen, the surface antigen, sAg, as well as the presurface sequences, pre-S1 and pre-S2 (formerly called pre-S), as well as combinations of the above, such as sAg/pre-S1, sAg/pre-S2, sAg/pre-S1/pre-S2, and pre-S1/pre-S2, will find use herein. See, e.g., "HBV Vaccines—from the laboratory to license: a case study" in Mackett, M. and Williamson, J. D., *Human Vaccines and Vaccination*, pp. 159–176, for a discussion of HBV structure; and U.S. Pat. Nos. 4,722,840, 5,098,704, 5,324,513, incorporated herein by reference in their entireties; Beames et al., *J. Virol.* (1995) 69:6833–6838, Birnbaum et al., *J. Virol.* (1990) 64:3319–3330; and Zhou et al., *J. Virol.* (1991) 65:5457–5464.

Antigens derived from other viruses will also find use in the claimed methods, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae (e.g., HTLV-I; HTLV-II; HIV-1 (also known as HTLV-III, LAV, ARV, hTLR, etc.)), including but not limited to antigens from the isolates $HIV_{IIIb}$, $HIV_{SF2}$, $HIV_{LAV}$, $HIV_{LAI}$, $HIV_{MN}$); HIV-$1_{CM235}$, HIV-$1_{US4}$; HIV-2; simian immunodeficiency virus (SIV) among others. Additionally, antigens may also be derived from human papillomavirus (HPV) and the tick-borne encephalitis viruses. See, e.g. Virology, 3rd Edition (W. K. Joklik ed. 1988); *Fundamental Virology*, 2nd Edition (B. N. Fields and D. M. Knipe, eds. 1991), for a description of these and other viruses.

More particularly, the gp120 envelope proteins from any of the above HIV isolates, including members of the various genetic subtypes of HIV, are known and reported (see, e.g., Myers et al., Los Alamos Database, Los Alamos National Laboratory, Los Alamos, N. Mex. (1992); Myers et al., *Human Retroviruses and Aids*, 1990, Los Alamos, N. Mex.: Los Alamos National Laboratory; and Modrow et al., *J. Virol.* (1987) 61:570–578, for a comparison of the envelope sequences of a variety of HIV isolates) and antigens derived from any of these isolates will find use in the present methods. Furthermore, the invention is equally applicable to other immunogenic proteins derived from any of the various HIV isolates, including any of the various envelope proteins such as gp160 and gp41, gag antigens such as p24gag and p55gag, as well as proteins derived from the pol region.

As explained above, influenza virus is another example of a virus for which the present invention will be particularly useful. Specifically, the envelope glycoproteins HA and NA of influenza A are of particular interest for generating an immune response. Numerous HA subtypes of influenza A have been identified (Kawaoka et al., *Virology* (1990) 179:759–767; Webster et al., "Antigenic variation among type A influenza viruses," p. 127–168. In: P. Palese and D. W. Kingsbury (ed.), *Genetics of influenza viruses*. Springer-Verlag, New York). Thus, proteins derived from any of these isolates can also be used in the immunization techniques described herein.

The methods described herein will also find use with numerous bacterial antigens, such as those derived from organisms that cause diphtheria, cholera, tuberculosis, tetanus, pertussis, meningitis, and other pathogenic states, including, without limitation, *Meningococcus* A, B and C,

*Hemophilus influenza* type B (HIB), and *Helicobacter pylori*. Examples of parasitic antigens include those derived from organisms causing malaria and Lyme disease.

Furthermore, the methods described herein provide a means for treating a variety of malignant cancers. For example, the system of the present invention can be used to mount both humoral and cell-mediated immune responses to particular proteins specific to the cancer in question, such as an activated oncogene, a fetal antigen, or an activation marker. Such tumor antigens include any of the various MAGEs (melanoma associated antigen E), including MAGE 1, 2, 3, 4, etc. (Boon, T. *Scientific American* (March 1993): 82–89); any of the various tyrosinases; MART 1 (melanoma antigen recognized by T cells), mutant ras; mutant p53; p97 melanoma antigen; CEA (carcinoembryonic antigen), among others.

It is readily apparent that the subject invention can be used to prevent or treat a wide variety of diseases.

The selected antigen is entrapped in, or adsorbed to, a microparticle for subsequent delivery. Biodegradable polymers for manufacturing microparticles useful in the present invention are readily commercially available from, e.g., Boehringer Ingelheim, Germany and Birmingham Polymers, Inc., Birmingham, Ala. For example, useful polymers for forming the microparticles herein include those derived from polyhydroxybutyric acid; polycaprolactone; polyorthoester; polyanhydride; as well as a poly($\alpha$-hydroxy acid), such as poly(L-lactide), poly(D,L-lactide) (both known as "PLA" herein), poly(hydoxybutyrate), copolymers of D,L-lactide and glycolide, such as poly(D,L-lactide-co-glycolide) (designated as "PLG" or "PLGA" herein) or a copolymer of D,L-lactide and caprolactone. Particularly preferred polymers for use herein are PLA and PLG polymers. These polymers are available in a variety of molecular weights, and the appropriate molecular weight for a given antigen is readily determined by one of skill in the art. Thus, e.g., for PLA, a suitable molecular weight will be on the order of about 2000 to 250,000. For PLG, suitable molecular weights will generally range from about 10,000 to about 200,000, preferably about 15,000 to about 150,000, and most preferably about 50,000 to about 100,000.

If a copolymer such as PLG is used to form the microparticles, a variety of lactide:glycolide ratios will find use herein and the ratio is largely a matter of choice, depending in part on the coadministered antigen and the rate of degradation desired. For example, a 50:50 PLG polymer, containing 50% D,L-lactide and 50% glycolide, will provide a fast resorbing copolymer while 75:25 PLG degrades more slowly, and 85:15 and 90:10, even more slowly, due to the increased lactide component. It is readily apparent that a suitable ratio of lactide:glycolide is easily determined by one of skill in the art based on the nature of the antigen and disorder in question. Moreover, mixtures of microparticles with varying lactide:glycolide ratios will find use in the formulations in order to achieve the desired release kinetics for a given antigen and to provide for both a primary and secondary immune response. Degradation rate of the microparticles of the present invention can also be controlled by such factors as polymer molecular weight and polymer crystallinity. PLG copolymers with varying lactide:glycolide ratios and molecular weights are readily available commercially from a number of sources including from Boehringer Ingelheim, Germany and Birmingham Polymers, Inc., Birmingham, Ala. These polymers can also be synthesized by simple polycondensation of the lactic acid component using techniques well known in the art, such as described in Tabata et al., *J. Biomed. Mater. Res.* (1988) 22:837–858.

The antigen/microparticles are prepared using any of several methods well known in the art. For example, double emulsion/solvent evaporation techniques, such as described in U.S. Pat. No. 3,523,907 and Ogawa et al., *Chem. Pharm. Bull.* (1988) 36:1095–1103, can be used herein to form the microparticles. These techniques involve the formation of a primary emulsion consisting of droplets of polymer solution containing the antigen (if antigen is to be entrapped in the microparticle), which is subsequently mixed with a continuous aqueous phase containing a particle stabilizer/surfactant.

More particularly, a water-in-oil-in-water (w/o/w) solvent evaporation system can be used to form the microparticles, as described by O'Hagan et al., *Vaccine* (1993) 11:965–969 and Jeffery et al., Pharm. Res. (1993) 10:362. In this technique, the particular polymer is combined with an organic solvent, such as ethyl acetate, dimethylchloride (also called methylene chloride and dichloromethane), acetonitrile, acetone, chloroform, and the like. The polymer will be provided in about a 2–15%, more preferably about a 4–10% and most preferably, a 6% solution, in organic solvent. An approximately equal amount of an antigen solution, e.g., in water, is added and the polymer/antigen solution emulsified using e.g, an homogenizer. The emulsion is then combined with a larger volume of an aqueous solution of an emulsion stabilizer such as polyvinyl alcohol (PVA) or polyvinyl pyrrolidone. The emulsion stabilizer is typically provided in about a 2–15% solution, more typically about a 4–10% solution. The mixture is then homogenized to produce a stable w/o/w double emulsion. Organic solvents are then evaporated.

The formulation parameters can be manipulated to allow the preparation of small (<5 $\mu$m) and large (>30 $\mu$m) microparticles. See, e.g., Jeffery et al., *Pharm. Res.* (1993) 10:362–368; McGee et al., *J. Microencap.* (1996). For example, reduced agitation results in larger microparticles, as does an increase in internal phase volume. Small particles are produced by low aqueous phase volumes with high concentrations of PVA.

Microparticles can also be formed using spray-drying drying and coacervation as described in, e.g., Thomasin et al., *J. Controlled Release* (1996) 41:131; U.S. Pat. No. 2,800,457; Masters, K. (1976) *Spray Drying* 2nd Ed. Wiley, N.Y.; air-suspension coating techniques, such as pan coating and Wurster coating, as described by Hall et al., (1980) The "Wurster Process" in *Controlled Release Technologies: Methods, Theory, and Applications* (A. F. Kydonieus, ed.), Vol. 2, pp. 133–154 CRC Press, Boca Raton, Fla. and Deasy, P. B., *Crit. Rev. Ther. Drug Carrier Syst.* (1988) S (2):99–139; and ionic gelation as described by, e.g., Lim et al., *Science* (1980) 210:908–910.

The above techniques are also applicable to the production of microparticles with adsorbed antigens. In this embodiment, microparticles are formed as described above, however, antigens are mixed with the microparticles following formation.

Particle size can be determined by, e.g., laser light scattering, using for example, a spectrometer incorporating a helium-neon laser. Generally, particle size is determined at room temperature and involves multiple analyses of the sample in question (e.g., 5–10 times) to yield an average value for the particle diameter. Particle size is also readily determined using scanning electron microscopy (SEM).

Prior to use of the microparticles, antigen content is generally determined so that an appropriate amount of the microparticles may be delivered to the subject in order to elicit an adequate immune response. Antigen content of the microparticles can be determined according to methods known in the art, such as by disrupting the microparticles and extracting the entrapped antigen. For example, microparticles can be dissolved in dimethylchloride and the protein extracted into distilled water, as described in, e.g., Cohen et al., *Pharm. Res.* (1991) 8:713; Eldridge et al., *Infect. Immun.* (1991) 59:2978; and Eldridge et al., *J. Controlled Release* (1990)11:205. Alternatively, microparticles can be dispersed in 0.1 M NaOH containing 5% (w/v) SDS. The sample is agitated, centrifuged and the supernatant assayed for the antigen of interest using an appropriate assay. See, e.g., O'Hagan et al., *Int. J. Pharm.* (1994) 103:37–45.

As explained above, a submicron oil-in-water emulsion formulation will also be administered to the vertebrate subject, either prior to, concurrent with, or subsequent to, delivery of the antigen/microparticle.

Submicron oil-in water emulsions for use herein include nontoxic, metabolizable oils and commercial emulsifiers. Examples of nontoxic, metabolizable oils include, without limitation, vegetable oils, fish oils, animal oils or synthetically prepared oils. Fish oils, such as cod liver oil, shark liver oils and whale oils, are preferred, with squalene, 2,6,10,15,19,23-hexamethyl-2,6,10,14,18,22-tetracosahexaene, found in shark liver oil, particularly preferred. The oil component will be present in an amount of from about 0.5% to about 20% by volume, preferably in an amount up to about 15%, more preferably in an amount of from about 1% to about 12% and most preferably from 1% to about 4% oil.

The aqueous portion of the adjuvant can be buffered saline or unadulterated water. Since the compositions are intended for parenteral administration, it is preferable to make up the final solutions so that the tonicity, i.e., osmolality, is essentially the same as normal physiological fluids, in order to prevent post-administration swelling or rapid absorption of the composition due to differential ion concentrations between the composition and physiological fluids. If saline is used rather than water, it is preferable to buffer the saline in order to maintain a pH compatible with normal physiological conditions. Also, in certain instances, it may be necessary to maintain the pH at a particular level in order to insure the stability of certain composition components. Thus, the pH of the compositions will generally be pH 6–8 and pH can be maintained using any physiologically acceptable buffer, such as phosphate, acetate, tris, bicarbonate or carbonate buffers, or the like. The quantity of the aqueous agent present will generally be the amount necessary to bring the composition to the desired final volume.

Emulsifying agents suitable for use in the oil-in-water formulations include, without limitation, sorbitan-based non-ionic surfactants such as those commercially available under the name of SPAN® or ARLACEL®; polyoxyethylene sorbitan monoesters and polyoxyethylene sorbitan triesters, commercially known by the name TWEEN®; polyoxyethylene fatty acids available under the name MYRJ®; polyoxyethylene fatty acid ethers derived from lauryl, acetyl, stearyl and oleyl alcohols, such as those known by the name of BRIJ®; and the like. These substances are readily available from a number of commercial sources, including ICI America's Inc., Wilmington, Del. These emulsifying agents may be used alone or in combination. The emulsifying agent will usually be present in an amount of 0.02% to about 2.5% by weight (w/w), preferably 0.05% to about 1%, and most preferably 0.01% to about 0.5. The amount present will generally be about 20–30% of the weight of the oil used.

The emulsions can also contain other immunostimulating agents, such as muramyl peptides, including, but not limited to, N-acetyl-muramyl-L-threonyl-D-isoglutamine (thr-MDP), N-actetyl-normuramyl-L-alanyl-D-isogluatme (nor-MDP), N-acetylmuramyl-L-alanyl-D-isogluatminyl-L-alanine-2-(1'-2'-dipalmitoyl-sn-glycero-3-huydroxyphosphoryloxy)-ethylamine (MTP-PE), etc. Immunostimulating bacterial cell wall components, such as monophosphorylipid A (MPL), trehalose dimycolate (TDM), and cell wall skeleton (CWS), may also be present.

For a description of various suitable submicron oil-in-water emulsion formulations for use with the present invention, see, e.g., International Publication No. WO 90/14837; *Remington: The Science and Practice of Pharmacy*, Mack Publishing Company, Easton, Pa., 19th edition, 1995; Van Nest et al., "Advanced adjuvant formulations for use with recombinant subunit vaccines," In *Vaccines 92, Modern Approaches to New Vaccines* (Brown et al., ed.) Cold Spring Harbor Laboratory Press, pp. 57–62 (1992); and Ott et al., "MF59—Design and Evaluation of a Safe and Potent Adjuvant for Human Vaccines" in *Vaccine Design: The Subunit and Adjuvant Approach* (Powell, M. F. and Newman, M. J. eds.) Plenum Press, New York (1995) pp. 277–296.

In order to produce submicron particles, i.e., particles less than 1 micron in diameter and in the nanometer size range, a number of techniques can be used. For example, commercial emulsifiers can be used that operate by the principle of high shear forces developed by forcing fluids through small apertures under high pressure. Examples of commercial emulsifiers include, without limitation, Model 110Y microfluidizer (Microfluidics, Newton, Mass.), Gaulin Model 30CD (Gaulin, Inc., Everett, Mass.), and Rainnie Minilab Type 8.30H (Miro Atomizer Food and Dairy, Inc., Hudson, Wis.). The appropriate pressure for use with an individual emulsifier is readily determined by one of skill in the art. For example, when the Model 110Y microfluidizer is used, operation at 5000 to 30,000 psi produces oil droplets with diameters of about 100 to 750 nm.

The size of the oil droplets can be varied by changing the ratio of detergent to oil (increasing the ratio decreases droplet size), operating pressure (increasing operating pressure reduces droplet size), temperature (increasing temperature decreases droplet size), and adding an amphipathic immunostimulating agent (adding such agents decreases droplet size). Actual droplet size will vary with the particular detergent, oil and immunostimulating agent (if any) and with the particular operating conditions selected. Droplet size can be verified by use of sizing instruments, such as the commercial Sub-Micron Particle Analyzer (Model N4MD) manufactured by the Coulter Corporation, and the parameters can be varied using the guidelines set forth above until substantially all droplets are less than 1 micron in diameter, preferably less than about 0.8 microns in diameter, and most preferably less than about 0.5 microns in diameter. By substantially all is meant at least about 80% (by number), preferably at least about 90%, more preferably at least about 95%, and most preferably at least about 98%. The particle size distribution is typically Gaussian, so that the average diameter is smaller than the stated limits.

Particularly preferred submicron oil-in-water emulsions for use herein are squalene/water emulsions optionally containing varying amounts of MTP-PE, such as the submicron oil-in-water emulsion known as "MF59" (International Publication No. WO 90/14837; Ott et al., "M F59—Design and Evaluation of a Safe and Potent Adjuvant for Human Vaccines" in *Vaccine Design: The Subunit and Adjuvant Approach* (Powell, M. F. and Newman, M. J. eds.) Plenum Press, New York, 1995, pp. 277–296). MF59 contains 4–5% w/v Squalene (e.g., 4.3%), 0.25–0.5% w/v TWEEN 80®, and 0.5% w/v SPAN 85® and optionally contains various amounts of MTP-PE, formulated into submicron particles using a microfluidizer such as Model 11 OY microfluidizer (Microfluidics, Newton, Mass.). For example, MTP-PE may be present in an amount of about 0–500 µg/dose, more preferably 0–250 µg/dose and most preferably, 0–100 µg/dose. MF59-0, therefore, refers to the above submicron oil-in-water emulsion lacking MTP-PE, while MF59-100 contains 100 µg MTP-PE per dose. MF69, another submicron oil-in-water emulsion for use herein, contains 4.3% w/v squalene, 0.25% w/v TWEEN 80®, and 0.75% w/v SPAN 85® an optionally MTP-PE. Yet another submicron oil-in-water emulsion is SAF, containing 10% squalene, 0.4% TWEEN 80®, 5% pluronic-blocked polymer L121, and thr-MDP, also microfluidized into a submicron emulsion.

Once the submicron oil-in-water emulsion is formulated it can be administered to the vertebrate subject, either prior to, concurrent with, or subsequent to, delivery of the microparticle. If administered prior to immunization with the microparticle, the adjuvant formulations can be administered as early as 5–10 days prior to immunization, preferably 3–5 days prior to immunization and most preferably 1–3 or 2 days prior to immunization with the antigens of interest. If administered separately, the submicron oil-in-water formulation can be delivered either to the same site of delivery as the microparticle compositions or to a different delivery site.

If simultaneous delivery is desired, the submicron oil-in-water formulation can be included with the microparticle compositions. Generally, the microparticles and submicron oil-in-water emulsion can be combined by simple mixing, stirring, or shaking. Other techniques, such as passing a mixture of the two components rapidly through a small opening (such as a hypodermic needle) can also be used to provide the vaccine compositions.

If combined, the various components of the composition can be present in a wide range of ratios. For example, the microparticle and emulsion components are typically used in a volume ratio of 1:50 to 50:1, preferably 1:10 to 10:1, more preferably from about 1:3 to 3:1, and most preferably about 1:1. However, other ratios may be more appropriate for specific purposes, such as when a particular antigen is both difficult to incorporate into a microparticle and has a low immungenicity, in which case a higher relative amount of the antigen component is required.

Once formulated, the compositions of the invention are administered parenterally, generally by injection. The compositions can be injected either subcutaneously, intraperitoneally, intravenously or intramuscularly. Dosage treatment may be a single dose schedule or a multiple dose schedule. A multiple dose schedule is one in which a primary course of vaccination may be with 1–10 separate doses, followed by other doses given at subsequent time intervals, chosen to maintain and/or reinforce the immune response, for example at 1–4 months for a second dose, and if needed, a subsequent dose(s) after several months. The boost may be with a microparticle/submicron oil-water-emulsion given for the primary immune response, or may be with a different formulation that contains the antigen. The dosage regimen will also, at least in part, be determined by the need of the subject and be dependent on the judgment of the practitioner. Furthermore, if prevention of disease is desired, the vaccines are generally administered prior to primary infection with the pathogen of interest. If treatment is desired, e.g., the reduction of symptoms or recurrences, the vaccines are generally administered subsequent to primary infection.

The compositions will generally include one or more "pharmaceutically acceptable excipients or vehicles" such as water, saline, glycerol, polyethyleneglycol, hyaluronic acid, ethanol, etc. Additionally, auxiliary substances, such as wetting or emulsifying agents, pH buffering substances, and the like, may be present in such vehicles.

The compositions will comprise a "therapeutically effective amount" of the antigen of interest. That is, an amount of antigen will be included in the compositions which, when in combination with the submicron-oil-in water emulsion, will cause the subject to produce a sufficient immunological response in order to prevent, reduce or eliminate symptoms. The exact amount necessary will vary, depending on the subject being treated; the age and general condition of the subject to be treated; the capacity of the subject's immune system to synthesize antibodies; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials. For example, for purposes of the present invention, an effective dose will typically range from about 1 µg to about 100 mg, more preferably from about 10 µg to about 1 mg, and most preferably about 50 µg to about 500 µg of the antigen delivered per dose.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Preparation of p24 Antigen-Entrapped Microparticles

Materials used to formulate the microparticles were as follows:

(1) poly(D,L-lactide-co-glycolide), 50:50 mol ratio lactide to glycolide, MW average=70–100 kDa (50:50 PLGA high viscosity polymer) (Medisorb Technologies International, Cincinnati, Ohio);

(2) 8% polyvinyl alcohol (PVA) 3-83 (Mowiol, Frankfurt, Germany) in water saturated 10% with ethyl acetate by adding 6 ml of the latter and stirring in a screw cap glass bottle for 10 minutes; and (3) p24gag/sf2, in 30 mM Tris, pH 7.5, at a concentration of 6.1 mg of antigen/ml with 20:1 sucrose:protein.

P24gag microparticles were prepared by a solvent extraction technique as follows. To make the microparticles, 2.58 g of the polymer solution was sonicated with 0.8 ml of the antigen solution for 30 seconds. The primary emulsion was homogenized with 60 grams of the saturated PVA solution using a benchtop homogenizer with a 20 mm probe at 10 K rpm for 1 minute. The resulting emulsion was immediately added to 2.5 L of water, stirred for two hours for solvent extraction, filtered through a 38 μmesh, washed by centrifugation 3 times, and a portion sonicated for one minute in a water bath sonicator, then sized by laser diffraction measurement. The mean diameter size of the microparticles was 10 μm. The microspheres were lyophilized and stored at −20° C.

EXAMPLE 2

Immungenicity of p24gag/sf2 Antigen-Entrapped Microparticles with MF59

10 Baboons were divided into two groups (five baboons per group) and administered the formulations specified in Table 1. For Group 1, equal parts of the adjuvant MF59-0, and p24gag/sf2 (in a citrate/Tris buffer) were combined to yield a total of 0.7 ml. The composition was gently mixed and 500 µl (to yield 100 µg p24gag/sf2/dose) of vaccine was injected intramuscularly (IM) in the thigh muscle. For Group 2, 1.5 ml of 2x phosphate buffered saline (PBS) was added to 46.8 mg of the PLG-entrapped p24gag/sf2 formulation produced in Example 1. The material was vortexed for about 30 seconds until all beads were in suspension. 1.5 ml of MF59-0 was added to the resuspended beads to yield a total of 3 ml. The composition was gently mixed and 500 µl (to yield 100 µg p24gag/sf2/dose) of vaccine was injected IM in the thigh muscle.

Both groups of animals were boosted twice at 4 week intervals following the initial injection, with 500 µl of the vaccine composition. Two weeks following the second boost (10 weeks after the initial immunization) serum was collected and IgG titers evaluated by a standard ELISA, essentially as described below.

As shown in Table 1, entrapped p24gag/sf2+MF59 elicited a significantly greater antibody response than nonentrapped p24gag/sf2+MF59.

TABLE 1

| Group/Formulation | Mean IgG titers |
|---|---|
| Group 1 | |
| p24gag/sf2 100 µg + MF59-0 | 19,976 |
| Group 2 | |
| p24gag/sf2 100 µg in PLG Microparticles + MF59-0 | 85,725 |

EXAMPLE 3

Preparation of qp120/sf2 Antigen-Entrapped Microparticles

Materials used to formulate the microparticles were as follows:

(1) 3.0 g of the polymer poly(D,L-lactide-co-glycolide) composed of a 50:50 mol ratio of lactide to glycolide with a molecular weight average of 80 Kdal, (Boehringer Ingelheim Resomer RG505), was dissolved in 50 ml of dichloromethane (DCM, HPLC grade, obtained from Aldrich);

(2) 16 g polyvinyl alcohol (13–23 Kdal molecular weight average, ICN Biomedicals, Aurora, Ohio) was dissolved in 200 ml deionized water; and (3) HIV gp120sf2 antigen (Chiron, clinical grade) was used, at a concentration of 7.2 mg antigen/ml in 30 mM sodium citrate, pH 6.0, buffer.

Microparticles were prepared as follows. 1.67 ml of the HIV gp120sf2 antigen were added to 16.7 ml of the poly (D,L-lactide-co-glycolide) solution in a 30 ml glass heavy-walled test tube. The solution was homogenized 3 minutes at 23,000 RPM using a small, hand-held homogenizer equipped with 10 mm diameter generator. The homogenate was then slowly poured into 66.8 ml of the polyvinyl alcohol solution in a 150 ml glass beaker while homogenizing at 12,000 RPM using a bench scale homogenizer equipped with a 20 mm diameter generator for a total homogenization time of 3 minutes. The beaker containing the resulting double emulsion was equipped with a small magnetic stir bar. This was then allowed to sit overnight at ambient temperature under moderate (approximately 1000 RPM) stirring rate to evaporate the DCM solvent. The resulting microparticles prepared in this way were washed to remove excess PVA and un-entrapped antigen. Washing was accomplished by repeatedly (3 times total) diluting the microparticle preparation in approximately 450 ml deionized water, centrifuging to pellet microparticles, decanting off supernatant, and resuspending the microparticles in approximately 30 ml deionized water. After the final resuspension step, the microparticles were lyophilized and stored at −20° C.

Small samples (10–30 mg) of the lyophilized microparticles were utilized to measure particle size distribution and antigen content. The size distribution of the microparticles thus prepared was measured by dynamic laser light scatter using a Malvern Mastersizer instrument and determined to have a median size of 0.6 µm. The antigen content (% load) was measured by dissolving samples of the microparticles in a 0.1 M sodium hydroxide, 1% sodium dodecyl sulfate solution, then measuring protein content using a standard bicinchoninic acid (BCA) assay (Pierce, Rockford, Ill.). The % load of the microparticles was measured in this manner and determined to contain 0.7% protein by weight.

EXAMPLE 4

Immungenicity of qp120/sf2 Antigen-Entrapped Microparticles with MF59 in Baboons A similar experiment was run as described in Example 2, using gp102/sf2 in place of p24gag/sf2. In particular, gp120/sf2 was combined with MF59-0 and 50 µg administered to Group 1 baboons, as described above. Additionally, the PLG-entrapped gp120/sf2 from Example 1 was combined with MF59-0 as described and 50 µg administered to the Group 2 animals.

Both groups of animals were boosted at 4 weeks following the initial injection, with 500 µl of the vaccine composition. Serum samples were collected four weeks after the initial dose (4wp1), as well as four weeks following the second dose (4wp2) and 8 weeks following the second dose (8wp2) and IgG titers evaluated by ELISA as follows. 96-well ELISA plates (Nunc U96, cat#449824) were coated with 100 µl per well of 2 µg/ml gp120/sf2 antigen in 50 mM sodium borate buffer, pH 9.0. The plates were incubated overnight at 4° C. Baboon serum samples, initially diluted 1:50 to 1:1000 in 100 mM sodium phosphate, 1 mM EDTA, 0.5 M sodium chloride buffer, pH 7.5 (dilution solution), were serially diluted with dilution solution 1:2 from top to bottom of the ELISA plate (one column per serum sample) such that samples were diluted by a factor of 1-, 2-, 4-, 8-, 16-, 32-, 64- and 128-fold greater than the initial dilution, with a final volume of 100 µl sample per well. A column containing dilution solution only (blank), and a standard serum (standard) were included on each plate for comparison purposes. ELISA plates were incubated 1 hour at 37° C. After washing plates extensively with 0.05% Triton-X100 solution, 100 µl per well of a 1:5000 diluted Goat anti-Monkey IgG-HRP conjugate solution (Organon Teknike Corp., West Chester, Pa., cat#55432) was added. Plates were incubated 1 hour at 37° C. Plates were again washed extensively with 0.05% Triton-X100. 100 µl TMB peroxide developer solution (Kirkegaard & Perry labs, Gaithersburg, Md.) were added to each well. Color reaction was allowed to develop for approximately 3 minutes before stopping by adding 50 µl per well 2 M HCl . Plates were read using an ELISA reader at 450 nm. Resulting OD values for each plate were subtracted from baseline OD using average values from a blank column. Titers for each serum sample were expressed as the dilution required to achieve an OD of 0.5 as determined by fitting resulting data to a log-logit function.

As shown in Table 2, entrapped gp120/sf2+MF59 elicited a greater antibody response than nonentrapped gp120/sf2+

MF59 in all groups with the response seen at four weeks after the first dose being significantly higher.

TABLE 2

| Group/Formulation | Mean IgG titers 4wp1 | Mean IgG titers 4wp2 | Mean IgG titers 8wp2 |
|---|---|---|---|
| Group 1 | | | |
| gp120/sf2 50 µg + MF59-0 | 10 | 3297 | 1118 |
| Group 2 | | | |
| gp120/sf2 50 µg entrapped in PLG Microparticles + MF59-0 | 637 | 5120 | 1733 |

EXAMPLE 5

Immungenicity of gp120/sf2 Antigen-Entrapped Microparticles with MF59 in Mice

The ability of HIV gp120 to stimulate an immune response when entrapped or adsorbed to PLG microparticles and coadministered with MF59 was also tested in mice as follows. Balb/C mice, 6–7 weeks in age, were divided into four groups and administered intramuscularly 50 µl of a vaccine composition containing 10 µg of HIV gp120, and adjuvant as specified in Table 3. The various compositions were prepared as described in Example 4 above.

TABLE 3

| Group | Animal numbers | Adjuvant Name | Dose | Antigen Name | Volume per Dose | Site | Injection Animal | Route |
|---|---|---|---|---|---|---|---|---|
| 1 | (10) | PBS | | HIV gP120 (soluble) | 10 µg | 50 µl | 50 µl | IM |
| 2 | (30) | MF59-0 | 25 µl | HIV gP120 (soluble) | 10 µg | 50 µl | 50 µl | IM |
| 3 | (30) | PLG/gp120 | 1.3 mg | HIV gP120 (entrapped) | 10 µg | 50 µl | 50 µl | IM |
| 4 | (30) | PLG/gp120 in MF59-0 | 1.3 mg 25 µl | HIV gP120 (entrapped) | 10 µg | 50 µl | 50 µl | IM |

Animals were boosted at 4 and 8 weeks following the initial injection. Serum was collected at 2, 6 and 10 weeks following injection and IgG titers evaluated by a standard ELISA, as described in Example 4.

The results are shown in Table 4 and FIG. 1. In all cases, IgG titers were higher in the group administered PLG-entrapped gp120+MF59 than IgG titers in the other groups, and significantly higher than the group administered MF59 alone. At 10 weeks following injection, IgG titers were significantly higher in the group adminstered PLG-entrapped gp120+MF59 as compared to all other groups.

TABLE 4

| Formulation | Total IgG | | |
|---|---|---|---|
| | 2 weeks | 6 weeks | 10 weeks |
| gp120 | 9 | 9 | 19 |
| gp120 + MF59 | 9 | 65 | 851 |
| PLG/gp120 | 54 | 40728 | 62167 |
| PLG/gp120 + MF59 | 82 | 70672 | 113172 |

EXAMPLE 6

Immungenicity of HCV E2 Antigen-Entrapped Microparticles with MF59 in Mice

The ability of the hepatitis C virus (HCV) E2 antigen to stimulate an immune response when entrapped or adsorbed to PLG microparticles and coadministered with MF59 was tested as follows. Mice were divided into six groups and administered intramuscularly 50 µl of a vaccine composition containing 5 µg of HCV E2 antigen and adjuvant as specified in Table 5. The compositions were prepared essentially as described above.

Animals were boosted at 4 and 8 weeks following the initial injection. Serum was collected at 2, 6, 10 and 12 weeks following injection and IgG titers evaluated by a standard ELISA, essentially as described above.

As shown in Table 6, antibody titers for HCV E2, either adsorbed or entrapped in PLG microparticles, and coadministered with MF59, were higher than those seen when PLG or MF59 were administered alone.

TABLE 5

| Group # | Adjuvant Name | Dose | E2 Dose |
|---|---|---|---|
| 1 | MF59 | 50 µl | — |
| 2 | PLG mixed | 500 µg | 5 µg |
| 3 | PLG adsorbed | 500 µg | 5 µg |
| 4 | PLG entrapped | 500 µg | 5 µg |
| 5 | PLG adsorbed + MF59 | 500 µg | 5 µg |
| 6 | PLG entrapped + MF59 | 500 µg | 5 µg |

TABLE 6

| Weeks | MF59 | PLG | PLG adsorbed | PLG entrapped | PLG ads. + MF59 | PLG entr. + MF59 |
|---|---|---|---|---|---|---|
| 0 | 0.43 | 0.39 | 0.42 | 0.5 | 0.47 | 0.52 |
| 2 | 0.37 | 0.21 | 0.19 | 0.28 | 2.26 | 0.54 |
| 6 | 31.48 | 4.71 | 5.67 | 49.96 | 98.77 | 175.69 |
| 10 | 155.04 | 6.74 | 31.35 | 176 | 418 | 425 |
| 12 | 141 | 1.13 | 20.33 | 21.66 | 123 | 188 |

Accordingly, the use of submicron oil-in-water emulsions with antigen-entrapped and -adsorbed microparticles is disclosed. Although preferred embodiments of the subject invention have been described in some detail, it is understood that obvious variations can be made without departing from the spirit and the scope of the invention as defined by the appended claims.

We claim:

1. A method of inducing an immune response which comprises administering to a vertebrate subject (a) a submicron oil-in-water emulsion immunological adjuvant, and (b) a therapeutically effective amount of a selected antigen entrapped in, or adsorbed to, a biodegradable microparticle, wherein the submicron oil-in-water emulsion comprises 1% to 12% by volume of a non-toxic metabolizable oil and 0.02% to 2.5% (w/v) of emulsifying agent.

2. The method of claim 1, wherein the microparticle is formed from a poly(α-hydroxy acid) selected from the group consisting of poly(L-lactide), poly(D,L-Iactide) and poly(D,L-lactide-co-glycolide).

3. The method of claim 2, wherein the microparticle is formed from poly(D,L-lactide-co-glycolide.

4. The method of claim 1, wherein the submicron oil-in-water emulsion comprises 4–5% w/v squalene, 0.25–0.5% w/v polyoxyethylene sorbitan monooleate, and 0.5% w/v sorbitan trioleate, and optionally, N-acetylmuramyl-L-alanyl-D-isogluatminyl-L-alanine-2-(1'-2'-dipalmitoyl-sn-glycero-3-hydroxyphosphoryloxy)-ethylamine.

5. The method of claim 1, wherein the selected antigen is a viral antigen.

6. The method of claim 5, wherein the selected antigen is gp 120.

7. The method of claim 5, wherein the selected antigen is p24gag.

8. The method of claim 5, wherein the selected antigen is hepatitis C virus E2.

9. The method of claim 1, wherein the selected antigen is entrapped in the microp article.

10. The method of claim 1, wherein the selected antigen is adsorbed to the microparticle.

11. The method of claim 1, wherein the submicron oil-in-water emulsion is administered prior to the microparticle.

12. The method of claim 1, wherein the submicron oil-in-water emulsion is administered subsequent to the microparticle.

13. The method of claim 1, wherein the submicron oil-in-water emulsion is administered substantially concurrently with the microparticle.

14. The method of claim 1, wherein the submicron oil-in-water emulsion further comprises N-acetylmuramyl-L-alanyl-D-isogluatminyl-L-alanine-2-(1'-2'-dipalmitoyl-sn-glycero-3-hydroxyphosphoryloxy)-ethylamine.

15. the method of claim 4, wherein the submicron oil-in-water emulsion further comprises N-acetylmuramyl-L-alanyl-D-isogluatminyl-L-alanine-2-(1'-2'-dipalmitoyl-sn-glycero-3-hydroxyphosphoryloxy)-ethylamine.

* * * * *